United States Patent [19]

Moss et al.

[11] Patent Number: 5,166,142
[45] Date of Patent: Nov. 24, 1992

[54] USE OF TYPE IA ANTIARRHYTHMIC AGENTS TO LOWER BLOOD LIPIDS

[75] Inventors: Arthur J. Moss, Rochester, N.Y.; William E. Boden, Westwood, Mass.

[73] Assignee: University of Rochester, Rochester, N.Y.

[21] Appl. No.: 712,510

[22] Filed: Jun. 10, 1991

[51] Int. Cl.$^5$ .................. A61K 9/22; A61K 31/715; A61K 31/20

[52] U.S. Cl. .................. 514/54; 514/57; 514/60; 514/210; 514/357; 424/440; 424/455

[58] Field of Search .............. 514/54, 57, 60, 560, 514/821, 408, 423; 424/440, 455; 260/293.9, 287

[56] References Cited

U.S. PATENT DOCUMENTS 3,864,347  2/1975  Gutzwiller et al. ............. 260/287
3,898,237  8/1975  Grethe et al. ............. 260/293.9

OTHER PUBLICATIONS

Surewicz et al; Biochem Pharmacol 32(9); 1983; 1467–1472; Abstract only.
The Expert Panel, *Arch. Intern. Med.* 148: 36–69 (1988).
J. C. Rosa, *Circulation* 81: 1721–1733 (1990).
S. Yusef et al., *JAMA* 260: 2259–2263 (1988).
Members of the Working Group on Management of Patients with Hypertension and High Blood Cholesterol, *Ann. of Intern. Med.* 144: 224 (1991).
J. T. Bigger et al., in *The Pharmacologic Basis of Therapeutics*, pp. 748–783, A. G. Gillman et al. (eds.), MacMillan, N.Y. (1985).
E. Carmeliet et al., in "Clinical Aspects of Life-Threatening Arrhythmias," H. M. Greenberg et al. (eds.), *Ann. N.Y. Acad. Sciences* 427: 1–15 (1984).
E. M. V. Williams, *J. Clin. Pharmacol.* 24: 129–147 (1984).
The Multicenter Diltiazem Post-Infection Trial (MDPIT) Research Group, *New Engl. J. Med.* 319: 385–392 (1988).
S. G. Young, *Circulation* 82: 1574–1594 (1990).
*The Merck Index* (11th ed.), S. Budaveri (ed.), Merck & Co., Inc., Rahway, N.J. (1989).
*Remington's Pharmaceutical Sciences* (16th ed.), A. Osol (ed.), Mack Publishing Co., Easton, Pa. (1980).
H. A. Tyroler, *Circulation* 76: 515–522 (1987).
Lipid Research Clinics Program, *JAMA* 251: 351–364 (1984).
W. T. Friedewald et al., *Clin. Chem.* 18:499–502 (1972).

*Primary Examiner*—Ronald W. Griffin
*Assistant Examiner*—Louise Leary
*Attorney, Agent, or Firm*—Merchant, Gould, Smith, Edell, Welter & Schmidt

[57] ABSTRACT

A method is provided to lower serum cholesterol, total triglycerides and/or apoprotein B in a human by administering an effective amount of one or more Type IA antiarrhythmic agents to said human.

17 Claims, No Drawings

USE OF TYPE IA ANTIARRHYTHMIC AGENTS TO LOWER BLOOD LIPIDS

BACKGROUND OF THE INVENTION

Guidelines developed by the National Cholesterol Education Program's Expert Panel on Detection, Evaluation, and Treatment of High Blood Cholesterol in Adults, as reported in *Arch. Intern. Med.*, 148, 36 (1988), identified elevated cholesterol and low-density lipoprotein cholesterol (LDL-C) concentrations as the major targets for cholesterol-lowering therapy. The importance of cholesterol reduction in patients with overtly manifest coronary artery disease cannot be overstated, since virtually every major epidemiologic study performed to date has shown a significant correlation between the level of serum cholesterol at the time of entry and the risk of subsequent coronary disease. For example, see J. C. Rosa, *Circulation*, 81, 1721 (1990).

The results of 22 randomized cholesterol-lowering clinical trials to reduce the risk of coronary heart disease indicate an average reduction of 23 percent in the risk of non-fatal myocardial infarction and cardiac death in treated compared with control patients. In particular, a 10 percent decrease in the cholesterol level was associated with a reduction of approximately 20 percent in the incidence of new coronary events (S. Yusef et al., *JAMA*, 260, 2259 (1988)).

Present therapeutic guidelines include the recommendation that cholesterol-lowering drugs should be considered when cholesterol and low density lioprotein-cholesterol (LDL-C) levels remain significantly elevated after six months of appropriate dietary therapy. For example, see "National Education Programs Working Group Report on the Management of Patients With Hypertension and High Blood Cholesterol," *Ann. of Intern. Med.*, 114, 224 (1991). Currently available hypolipidemic agents include bile acid sequestrants (cholestyramine and cholestipol), nicotinic acid, probucol, fibric acid derivatives (gemfibrizol and clofibrate), HMG-CoA reductase inhibitors, and the omega-3 unsaturated fatty acids found in various fish oil supplements. To date, no other classes of lipid-lowering agents have been approved for clinical use.

However, these agents have been associated with side effects that can deter or preclude their usage by many patients. For example, colestyramine and cholestipol are associated with constipation and abdominal discomfort. Cholestyramine can cause vitamin K, A and D deficiencies. Probucol clofibrate and gemfibrizol can cause diarrhea, abdominal pain and nausea, and the first two agents have been associated with arrhythmias.

Therefore, a need exists for new agents which are effective to lower blood cholesterol total triglycerides and/or LDL-C.

SUMMARY OF THE INVENTION

The present invention provides a therapeutic method to lower serum lipids or lipid components selected from the group consisting of cholesterol, total triglycerides, apoprotein B and or low-density lipoprotein-cholesterol (LDC-C) comprising administering to a mammal in need of such treatment an effective amount of at least one type IA antiarrhythmic agent. Preferred type IA antiarrhythmic agents for use in the present method include quinidine, procainamide, disopyramide (including the pharmaceutically acceptable salts thereof) and mixtures thereof. The pharmaceutically acceptable salts thereof include the addition salts of inorganic and organic acids, some of which are commercially available, such as the phosphate, hydrochloride, sulfate, gluconate, galacturonate, polygalacturonate, dihydrobomide trihydrate, and methiodide monohydrate salts.

However, as used herein, the term "type IA antiarrhythmic agent" is not limited to these three discrete chemical moieties and their salts, but includes the derivatives and analogs thereof, which are recognized by the art to function as Type IA antiarrhythmic agents. A number of such derivatives have been disclosed in the patent and scientific literature, and are discussed in detail hereinbelow.

Although, for reasons such as the need to minimize side effects, and the need to simplify the administration schedule, the use of a single Type IA agent is preferred, the administration of a plurality, e.g., 2-5, of such agents is within the scope of the invention, and may be useful to manage lipid levels in certain refractory patients.

Antiarrhythmic or "antidysrhythmic" agents are frequently prescribed to patients with coronary heart disease and associated cardia arrhythmias. Presently, antiarrhythmic agents are classified by their presumed mechanism of action at the myocellular level. All Type I antiarrhythmic agents are characterized by their blocking effect on fast inward sodium current (J. T. Bigger et al., in *The Pharmacologic Basis of Therapeutics*, A. G. Gillman et al., eds., MacMillan, N.Y. (1985) at 748–783). The presently available Type I agents (quinidine, procainamide, disopyramide, lidocaine, tocainide, mexilitine, flecainide, encainide, and the recently released moricizine and propafenone) differ in the way they interfere with the sodium channel (potential and frequency dependent block), in their effects on other myocellular ionic channels, and in their binding characteristics to cardiac membranes (E. Carmeliet et al., in *Clinical Aspects of Life-Threatening Arrhythmias*, H. M. Greenberg et al., eds., *Ann. N.Y. Acad. Sciences*, 427, 1 (1984)). On the basis of the differences in the electrophysiologic and pharmacodynamic properties of the Type I agents, they have been subclassified into Type IA (quinidine, procainamide and disopyramide), Type IB (lidocaine, tocainide, mexilitine), and Type IC (flecainide, encainide, propafenone) subgroups by E. M. V. Williams, *J. Clin. Pharmacol.*, 24, 129 (1984).

As part of the multicenter diltiazem post-infarction trial (MDPIT), reported in *New Engl. J. Med.*, 319, 385 (1988), we prospectively collected serial blood samples for lipid and apoprotein determinations and recorded the concomitant cardiac medications the patients were receiving. The effect of various cardiac medications on the blood lipids of the patients was then retrospectively evaluated. We unexpectedly found that Type IA antiarrhythmic agents were associated with a meaningful and significant reduction in total cholesterol, triglycerides, and apoprotein B (Apo B). Apo B is the essential protein constituent of LDL (S. G. Young, *Circulation*, 82, 1574 (1990)), and in fact, LDL-C levels were also significantly lowered by the present method.

Total serum cholesterol was reduced about 5–15% over the course of the study as compared with patients not treated with the type IA agents. Total triglycerides were reduced about 12–35% and apoprotein B was reduced about 7.5–20%. Of course, longer courses of medication and/or higher doses may enhance the therapeutic effect of a given Type IA antiarrhythmic agent.

However, quinidine, procainamide and disopyramide were substantially equivalent in their effectiveness, within the variation of the assay methods.

In the study reported in Example 1, the course of treatment evaluated was 30 months. However, substantial lipid lowering was observed after 6 months, and shorter courses of treatment are likely to be effective.

Type IA antiarrythmic agents are also effective to lower said serum lipids or lipid components when administered in unit dosages or in daily dosages that are substantially less than the unit dosages (or daily dosages) conventionally employed to achieve antiarrythmic effects. Such unit dosage forms comprise about 25-50% of the amount of the Type IA antiarrythmic agent or agents that are conventionally provided, e.g., via a capsule, tablet, injectable dosage or the like. Therefore, the present invention also provides a pharmaceutical unit dosage form comprising an amount of a Type IA antiarrhythmic agent which is effective to lower the serum concentration of said lipid or lipid components recited above, which amount is substantially less than that which is employed to exert antiarrythmic effects. The amounts which are employed to exert antiarrythmic effects are extensively defined and discussed below.

DETAILED DESCRIPTION OF THE INVENTION

Preferred Type IA antiarrhythmic agents (or "drugs") for use in the present invention include quinidine, procainamide and disopyramide, as well as the salts, derivatives and analogs thereof that retain the Type IA profile of antiarrhythmic bioactivity, e.g., that have substantially similar electrophysiologic and pharmacodynamic properties. See E. M. V. Williams, cited supra.

1. Quinidine

Quinidine (6'-methoxycinchonan-9-ol) has the formula:

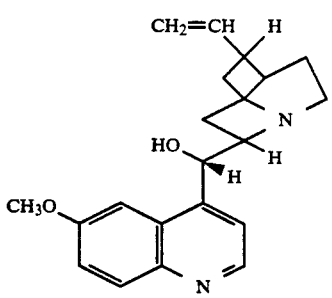

Its preparation, properties and salts (acid sulfate tetrahydrate, sulfate, hydrochloride monohydrate, dihydrobromide dihydrate, methiodide monohydrate, gluconate and polygalacturonate) are extensively discussed in *The Merck Index*, S. Budaveri, ed., Merck & Co., Inc., Rahway, N.J. (11th ed. 1989) at pages 8068-8068 (hereinafter, "*Merck*"), and in *Remington's Pharmaceutical Sciences*, A. Osol, ed., Mack Publishing Co., Easton, Pa. (16th ed. 1980) at pages 800-801 (hereinafter "*Remington's*").

Dosage forms of quinidine glucuronate which are available include an 80 mg/ml injectable form and 324 mg extended release tablets. Dosage forms of quinidine sulfate which are available include: capsules: 100, 200, and 300 mg; injection: 200 mg/ml; tablets: 100, 125, 200, and 300 mg; sustained-release tablets: 300 mg.

A number of commercially available proprietary unit dosage forms of quinidine are available. For example, quinidinine gluconate is available as Duraquin ®(330 mg sustained-release tablets) from Parke-Davis, Morris Plains, N.J.; quinidine polyglacturonate is available as Cardioquin ® (275 mg tablets) from The Purdue Frederick Co., Norwalk, Conn.; quinidine sulfate is available in 200 mg tablets from Lederle Laboratories, Wayne, N.J.

Oral adult dosages are up to 100-600 mg 3-6 times a day; infants and children, 6 mg/kg five times a day.

Analog and derivatives of quinidine which can be used in the present invention include compounds of the formula:

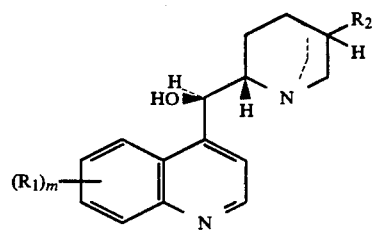

wherein m is 1 or 2; $R_1$ is hydrogen, hydroxy, halogen, trifluoromethyl, $(C_1-C_4)$alkyl, $(C_1-C_4)$alkoxy, or when m is 2, with an adjacent $R_1$, is also methylenedioxy; and $R_2$ is ethyl or vinyl. See, for example, U.S. Pat. Nos. 3,864,347 and 3,898,237.

2. Procainamide

Procainamide hydrochloride (4-amino-N-[2-(diethylamino)ethyl]benzamide monohydrochloride has the formula:

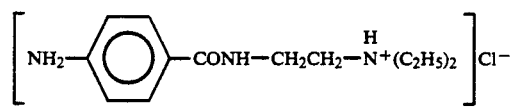

Free procainamide can be prepared by condensing p-nitrobenzoyl chloride with β-diethylaminoethylamine and then reducing the nitro group to amino by conventional methodology. The hydrochloride is formed by passing HCl into a solution of procainamide in an appropriate organic solvent. Other useful acid addition salts can be formed by reaction of the free base with the appropriate acid.

Procainamide and its dosage forms are discussed extensively in *Merck* at page 7759 and in *Remington's* at pages 799-800.

Dosage forms of procainamide-HCl which are available include capsules: 250, 375 and 500 mg; injection: 100 and 500 mg/ml; tablets 250, 375 and 500 mg. Procainamide-HCl capsules are available (250, 375 and 500 mg) from Lederle Laboratories.

Useful adult dosages range from 250-500 mg twice a day to 500 mg to 1.0 g every 4-7 hours, to 3.0-4.5 g doses administered once daily, taken orally. Procainamide can also be infused intravenously, e.g., 200 mg-1 g can be infused at 25-50 mg/min in an appropriate intravenous solution.

Useful derivatives and analogs of procainamide include compounds of the general formula:

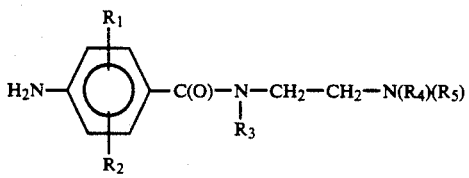

wherein $R_1$ and $R_2$ are individually H, OH, Cl or O(C$_1$-C$_3$)alkyl; $R_3$ is (C$_1$-C$_3$)alkyl, acetyl, 2-pyridyl, hydroxy or benzyl; $R_4$ is (C$_1$-C$_3$)alkyl and $R_5$ is (C$_1$-C$_3$)alkyl or p-chlorobenzyl, and the pharmaceutically acceptable salts thereof.

3. Disopyramide

Disopyramide (α-[2-bis(1-methylethyl)amino]ethyl]-α-phenyl-2-pyridineacetamide) has the formula:

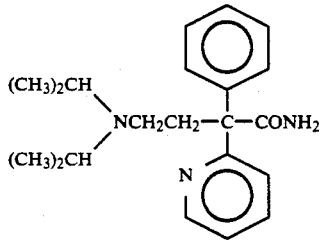

Disopyramide is prepared by heating 4-diisopropylamino-2-phenyl-2-(2-pyridyl)butyronitrile with concentrated sulfuric acid to convert it into the amide (*Chem. Abstr.*, 58, 12522e (1963)). Disopyramide and its phosphate salt are discussed extensively in Merck at pages 3360-61 and in *Remington's* at page 799. Dosage forms of disopyramide phosphate include 100 and 150 mg capsules. It is typically administered orally to adults at 100-200 mg every 6 hours. Disopyramide capsules are available from Lederle Laboratories.

Other useful analogs of disopyramide include those wherein the phenyl ring is replaced by tolyl, xylyl, naphthyl, halophenyl, anisyl and dimethoxyphenyl and/or the pyridine ring is substituted with halo, preferably chloro. See U.S. Pat. No. 3,225,054.

As noted above, the Type IA antiarrhythmic agents can be administered singly or in combination, and are effective to lower blood lipids when administered in daily dosages essentially equivalent to those employed to achieve antiarrhythmic effects. Although oral administration in tablets or capsules is preferred, parenteral routes of administration are also effective, and include, for example, injection and intravenous administration of the agents, in combination with a suitable liquid vehicle.

In the study that led to the present invention, patients ingested 150-600 mg/day of disopyramide orally in unit dosages of 150 mg or 100 mg; procainamide was orally administered at about 1.0-4.5 g/day in individual doses of 500 mg-3.0 g, and quinidine was orally administered at about 400 mg-2.0 g./day at individual doses of 200 mg-650 mg.

The invention will be further described by reference to the following detailed example.

EXAMPLE 1

A. Methodology

1. Study Population

The study population consisted of 1567 survivors of the original cohort of 2466 post-infarction patients enrolled in the Multicenter Diltiazem Post-Infarction Trial on whom lipid and lipoprotein specimens were obtained at study termination. The details of patient recruitment, data acquisition, data management, and follow-up have been previously reported, in *New Engl. J. Med.*, 319, 385 (1988). Patients were randomly assigned to diltiazem or placebo and were followed at periodic intervals throughout the trial. All patients were followed for at least 12 months, to a maximum of 52 months; the average duration of follow-up was 25 months.

2. Blood Samples for Lipid Assays

Venous blood was collected at baseline prior to randomization to trial medication, at approximately 6 months after entry into the study (range 3-12 months), and as part of the closeout procedure at study termination (average 30 months). An attempt was made to collect blood in the fasting state, but this was not universally accomplished due to logistical complexity.

The blood from each collected venous sample was allowed to clot at room temperature (30 min. to 2 hours), and serum was separated by low speed centrifugation (1500 XG for 15 minutes). Sera were initially frozen at $-20°$ C. at each participating center and shipped on dry ice to the Miriam Hospital Core Lipid Laboratory in Providence, R.I. where the sera were stored at $-70°$ C. until analysis. The baseline and 6 month sera samples were stored for 2-6 months before analysis, whereas the closeout samples were shipped immediately after acquisition to the Core Lipid Laboratory and analyzed promptly (within 2 weeks).

3. Analytic Methods for Serum Lipids

Serum cholesterol and triglyceride concentrations were determined on a Gilford System 3500 Computer Directed Analyzer by the methods of C. C. Allain et al. *Clin. Chem.*, 20, 470 (1973) and G. Bucolo et al., *Clin. Chem.*, 19, 476 (1973), respectively. High density lipoprotein-cholesterol (HDL-C) values were determined using methods identical to those of the Lipid Research Clinics program, as described in *Manual of Lipoprotein Operations*, Vol. 1, Dept. of HEW, Publication No. (NIH) 75-628 (1974), with the exception that the isopropanol and zeolite extraction steps are not required with the enzymatic methods.

Apoprotein A-I (Apo A-I) and apoprotein A-II (Apo A-II) levels were measured by validated double antibody radioimmunoassay techniques, as disclosed by M. C. Cheung, *J. Clin. Invest.*, 60, 43 (1977). Apoprotein B (Apo B) levels were determined by both a radioimmunoassay (RIA), as described by J. J. Albers et al., *Metabolism*, 24, 1339 (1975) and by a radial immunodiffusion assay (RID) (Fahey et al., *J. Immunol.*, 94, 84 (1965). There was a high degree of correlation between these two methods in normal subjects (114 mg./dl$\pm$31 vs. 119 mg/dl$\pm$33, respectively), but the radial immunodiffusion assay was, on average, 23 mg./dl higher than the radioimmunoassay in subjects with hypertriglyceridemic serum. Apo B levels declined by 20 percent during 36-week storage at $-20°$ C., with a smaller decline over time with storage at −70° C. Because of the decline in Apo B with prolonged storage, Apo B levels are reported only for closeout samples where the serum was analyzed within 2 weeks of collection.

4. Medication Usage

The cardiac medications that the patients were receiving were identified at baseline, at each follow-up contact, and at closeout utilizing a prespecified medication dictionary. The medication categories included antiarrhythmic agents, beta blockers, digitalis preparations, diuretic agents, nitrates other than sublingual preparations, and the trial medication (diltiazem or placebo). Each category was subcategorized for specific agents. At close out, 76 patients were on Type IA antiarrhythmic medication (41 were on various quinidine preparations, 29 were on procainamide, and 6 were on disopyramide). Twenty-seven patients were on a variety of other Type I antiarrhythmic agents (21 on Type IB and 6 on Type IC) and these agents had no apparent effect on serum lipids. No patient was on moricizine, which can also be classified as a Type IA antiarrhythmic agent.

5. Statistical Analyses

The difference in the group mean values of cholesterol, HDL-C, triglycerides, Apo A-I, Apo A-II, Apo B by RIA, and Apo B by RID for patients receiving and not receiving Type IA antiarrhythmic agents was evaluated by the two-sided t test. Stepwise Multiple linear regression analyses (BMDP-R computer program, in W. J. Dixon, ed., BMDP *Statistical Software Manual*, Vol. 1, U. of Cal. Press, Berkeley (1990) at pages 359–394, were performed to adjust for demographic, clinical, and therapeutic covariates that might influence the serum lipid levels. For each lipid fraction, a regression model was developed involving selected dichotomized covariates that had an influence (p<0.05) on the serum lipid level. Antiarrhythmic medication was then stepped-up into the model to evaluate the magnitude and significance of its independent effect on the lipid level, i.e., after adjustment for relevant covariates.

The reported analyses utilized the MDPIT analytic data base released Dec. 19, 1989.

B. Results

The clinical characteristics of the 1567 patients who had serum lipids obtained at closeout, subdivided by utilization of Type IA antiarrhythmic medication at study termination, are presented in Table 1.

TABLE 1

Baseline and Follow-Up Clinical Characteristics Of 1567 Patients With Serum Lipids Obtained At Closeout

| Characteristic | Total Population (N = 1567) | Type IA Antiarrhythmic Use | |
|---|---|---|---|
| | | No (N = 1491) | Yes (N = 76) |
| BASELINE | | | |
| Mean age (yr) | 58 ± 9.6 | 58 ± 9.6 | 58 ± 9.3 |
| <60 | 51 | 51 | 46 |
| Sex (M/F) | 80/20 | 80/20 | 89/11‡ |
| Cardiac history | | | |
| Previous myocardial infarction | 17[1] | 16 | 21 |
| NYHA Class II-IV* | 14 | 14 | 17 |
| Treatment for hypertension | 37 | 36 | 49‡ |
| Coronary bypass | 5 | 5 | 9 |
| surgery | | | |
| Insulin-dependent diabetes mellitus | 6 | 6 | 8 |
| Cigarette smoking | 47 | 47 | 39 |
| Cardiac findings | | | |
| Shock before enrollment | 3 | 3 | 5 |
| Pulmonary rales > bibasilar | 4 | 4 | 9‡ |
| Pulmonary congestion+ | 16 | 16 | 19 |
| Creatine kinase > 1000 Units | 52 | 51 | 57 |
| Blood urea nitrogen > 35 | 5 | 5 | 4 |
| Systolic blood pressure < 100 mmHg | 4 | 4 | 1 |
| Type & Location of acute infarction | | | |
| Antero-lateral Q-wave | 31 | 30 | 41 |
| Inferior-posterior Q-wave | 43 | 43 | 38 |
| Non-Q-wave | 25 | 25 | 21 |
| Radionuclide ejection fraction | | | |
| Mean | 48 ± 13.0 | 49 ± 12.9 | 42 ± 13.8‡ |
| ≧0.40 | 76 | 77 | 57 |
| Ambulatory electrocardiogram | | | |
| Mean Heart Rate (beats/min) | 71 ± 11.8 | 71 ± 11.7 | 71 ± 12.8 |
| AT CLOSEOUT | | | |
| Mean Weight (lbs) | 178 ± 33 | 177 ± 34 | 180 ± 31 |
| Medications | | | |
| Diltiazem | 47 | 47 | 37 |
| Beta Blockers | 52 | 53 | 41‡ |
| Digitalis | 11 | 10 | 41‡ |
| Diuretics | 28 | 28 | 39‡ |
| Nitrates other than sublingual | 33 | 33 | 41 |

[1]Figures are percentages unless otherwise indicated; plus minus values are mean ± SD.
*New York Heart Association functional classification one month before entry.
+Pulmonary congestion (x-ray) categorized as mild, moderate, or severe.
‡p < 0.05.

Patients receiving Type IA antiarrhythmic agents were more likely to be males with a history of hypertension, pulmonary rales during the index myocardial infarction, a reduced radionuclide ejection fraction, and frequent and repetitive ventricular ectopics on the ambulatory electrocardiogram, than those not on these agents. Digitalis and diuretics were more frequently utilized by the patients on antiarrhythmic agents than those not receiving Type IA medications, whereas the reverse was true for beta blockers. Randomized diltiazem therapy had no effect on the closeout blood cholesterol (diltiazem: cholesterol=227±47 mg/dl; placebo: cholesterol=226±47 mg/dl; t=0.39; p=0.70) or the various lipid fractions.

The total cholesterol levels at baseline and at 6 months and 20 months after infarction by antiarrhythmic use at the respective contacts are presented in Table 2.

TABLE 2

Cholesterol Levels at Three Contact Times By Type IA Antiarrhythmic Medication Use

| Time | Total Population | Type IA Antiarrhythmic Medication Use* | | Reduction in Cholesterol+ (percent) |
|---|---|---|---|---|
| | | No | Yes | |
| Baseline (N = 471) | 165 ±47 | 166 ±46 | 151 ±55 | 9.0 |
| 6-month contact (N-1130) | 207 ±48 | 208 ±49 | 190 ±39 | 8.7 |
| 30-month contact (N-1567) | 226 ±47 | 228 ±47 | 203 ±42 | 11.0 |

*Figures are mean serum cholesterol concentrations ± SD in mg/dl.
+Percent reduction in cholesterol for patients receiving Type IA antiarrhythmic agents compared to those not receiving these medications.

As shown by the data summarized in Table 2, the cholesterol level progressively increased during follow-up, but the cholesterol level was lower (8.7–11%) at each contact for those receiving Type IA antiarrhythmic agents, compared to those who were not.

The effects of Type IA antiarrhythmic medication taken as a whole as well as the effect of quinidine, procainamide, and disopyramide individually on the various lipid fractions at closeout, are presented in Table 3.

TABLE 3

Effect of Type IA Antiarrhythmic Medication on Various Lipid Fractions at Closeout

| Lipid Fraction | Type IA Antiarrhythmic Agents | | Specific Type IA Antiarrhythmic Agents | | |
|---|---|---|---|---|---|
| | No (N = 1491) | Yes (N = 76) | Quinidine (N = 41) | Procainamide (N = 29) | Disopyramide (N = 6) |
| Cholesterol | 228[1] ±47 | 203‡[2] ±42 | 201‡ ±39 | 207 ±48 | 194 ±39 |
| HDL-Cholesterol | 38 ±11 | 37 ±12 | 36 ±9 | 39 ±17 | 39 ±8 |
| Triglycerides | 228 ±150 | 197 ±197 | 212 ±247 | 177* ±89 | 195 ±218 |
| Apo A-I | 116 ±26 | 108 ±27 | 108 ±24 | 107 ±30 | 114 ±24 |
| Apo A-II | 28 ±8 | 24‡ ±6 | 24 ±5 | 24* ±6 | 30 ±11 |
| Apo B (RIA) | 121 ±29 | 105‡ ±28 | 105+ ±26 | 106 ±31 | 94 ±31 |
| Apo B (RID) | 121 ±29 | 104‡ ±28 | 103‡ ±23 | 108 ±34 | 87* ±21 |

[1]Figures are mean serum lipid concentrations ± SD in mg/dl.
[2]P values relate to comparisons between the indicated value and the value in the 1491 patients on no Type IA antiarrhythmic agents: *p < 0.01, +p < 0.001, ‡ p < 0.0001.

The Type IA medications were associated with a 14 percent reduction in Apo B level (p<0.0001) by both RIA and RID determinations, a 14 percent reduction in triglycerides (p=0.18), a 13 percent reduction in Apo A-II level (p<0.0001), an 11 percent reduction in total cholesterol (p<0.0001), a modest 6 percent reduction in Apo A-I level (p<0.02), and no meaningful effect on HDL-C. Quinidine, procainamide, and disopyramide were associated with similar reductions in cholesterol, triglycerides Apo A-II, and Apo B levels (Table 3). Multiple linear regression analyses (Table 4) indicate that Type IA antiarrhythmic agents were associated with significant reductions in cholesterol, triglycerides, Apo A-II, and Apo B that were independent of age, gender, diabetes, smoking status, concomitant medications, and a variety of clinical factors relating to the severity of the index coronary event.

TABLE 4

Magnitude and Significance of Lipid Reductions by Type IA Antiarrhythmic Agents on Closeout Blood Sample After Adjustment for Relevant Clinical Variables*

| Model | Lipid Fraction | Percent Reduction by Type IA Agents | 95% Confidence Limits | t Score | P Value |
|---|---|---|---|---|---|
| 1. | Cholesterol | 8.6 | 4.0, 13.0 | 3.64 | <0.0003 |
| 2. | Triglycerides | 22.3 | 11.4, 31.9 | 3.75 | <0.0002 |
| 3. | HDL-C | −1.4+ | −8.1, 4.9 | 0.42 | 0.67 |
| 4. | Apo A-I | 6.2 | 0.9, 11.2 | 2.29 | 0.02 |
| 5. | Apo A-II | 10.1 | 3.9, 15.9 | 3.13 | <0.001 |
| 6. | Apo B (RIA) | 12.7 | 7.1, 18.1 | 4.23 | <0.0001 |
| 7. | Apo B (RID) | 14.8 | 9.4, 19.9 | 5.09 | <0.0001 |

*Stepwise multiple linear regression analyses were performed to adjust for relevant covariates. For each lipid fraction, a regression model was developed in which all dichotomized variables from Table 1 that had an influence (p < 0.05) on the lipid fraction were included in the model. Type IA antiarrhythmic agents were then stepped into the covariate model to determine the independent effect that Type I agents had on the specified lipid fraction.
+The negative sign indicates an elevation in HDL-C.

C. DISCUSSION

Type IA antiarrhythmic agents are associated with significant reductions in total cholesterol, triglycerides, Apo A-II, and Apo B fractions. There was no significant effect of Type IA antiarrhythmic agents on HDL-C or Apo A-I levels. The magnitude of the lipid-lowering effect of Type IA antiarrhythmic agents on serum total cholesterol was approximately 9 percent, and the percent reduction in total cholesterol was similar at three different cholesterol levels, as shown on Table 2.

It should be emphasized that in the postinfarction secondary prevention trial, patients were not selected for trial entry according to any specific inclusion or exclusion criteria for blood lipids. The level of total cholesterol observed in this otherwise unselected post-infarction population was only minimally elevated. For example, the mean total cholesterol for the 1491 patients not receiving Type IA antiarrhythmic therapy at study closeout was 228±47 mg/dl—a value which would be considered "borderline-high" (200 to 239 mg/dl) by the National Cholesterol Education Program, cited supra.

The 9 percent reduction in cholesterol by Type IA antiarrhythmic agents observed in this study is in the range reported in major clinical trials using presently approved agents (see H. A. Tyroler, Circulation, 76, 515 (1987)). For example, in the Lipid Research Clinics Coronary Primary Prevention Trial (CPPT), poor patient compliance precluded attaining the targeted 25-30 percent cholesterol lowering effect, which would have been expected had patients been able to tolerate the maximum dosage of cholestyramine. Only a 9 percent reduction of cholesterol was achieved in the CPPT despite the extensive use of counseling by adherence counselors, as well as physicians (JAMA, 251, 351 (1984)). Yet this modest decrease of cholesterol was associated with a significant reduction in the incidence of new coronary events. Thus, the magnitude of reduction we observed in total cholesterol (9%), and Apo B concentration (13%) with Type IA antiarrhythmic agents is consonant with the effects achieved with approved hypolipidemic agents as used in a variety of drug trials.

LDL, the major cholesterol carrying particle in serum, has a lipid core and a single surface apoprotein, Apo B-100, as reported by S. G. Young, Circulation. 82, 1574 (1990). An elevated level of LDL-C is a major risk factor for the premature development of coronary atherosclerotic disease, and there is considerable interest in lowering LDL-C by diet and medication. LDL-C is usually computed from directly measured total cholesterol, HDL-C, and triglyceride values, as reported by W. T. Friedewald et al., Clin. Chem., 18, 499 (1972). The accuracy of this computation assumes a fasting blood sample and a fixed ratio of triglyceride to cholesterol in the triglyceride-rich lipoprotein moieties. We calculated the LDL-C concentrations, but did not report the findings because all blood samples were not drawn in the fasting state, and because of potential inaccuracies in the Friedewald assumptions. Despite these reservations, the calculated LDL-C level was significantly ($p=0.003$) lower among those receiving Type IA antiarrhythmic agents (LDL-C=$127\pm47$ mg./dl) than those not on these medications (LDL-C=$145\pm45$ mg/dl) at closeout. This computed 12 percent reduction in LDL-C is internally consistent with the independently measured 13 percent reduction in Apo B.

Type IA agents also lowered the concentration of Apo A-II, an important component of HDL, yet the HDL-C concentration was not affected by these agents (Table 3). The exact role of Apo A-II in the composition of HDL is unclear. HDL has considerable particle heterogeneity, some subfractions of HDL contain no Apo A-II, and Apo A-II is not an essential core protein of HDL. Thus, Apo A-II reduction can occur without concomitant lowering of HDL-C.

A hypolipidemic effect was not observed in the 21 patients on Type IB antiarrhythmic agents at closeout (cholesterol: IB no=$227\pm47$ mg/dl; IB yes=$221\pm49$ mg/dl; $t=0.56$, $p=0.58$). The reason for the differential hypolipidemic effects between Type IA and Type IB agents is unknown.

A major concern is that patients selected for therapy with Type IA antiarrhythmic agents in the study might have had lower cholesterol levels as a result of confounding factors such as diet, the severity of the cardiac disease, and the effects of concomitant medication. In an attempt to control for this, we carried out multiple linear regression analyses adjusting for a large number of measured clinical variables. Even after adjustment, the Type IA agents were associated with significant ($p<0.001$) reductions (>10%) in total cholesterol, triglyceride Apo A-II, and Apo B levels. Of course, covariates could not be adjusted that were not measured. It would be noted that at 22 months post-infarction, the average weight of the patients receiving Type IA antiarrhythmic agents was slightly greater than those not on these agents. This finding rules against a major disparity in diet, caloric intake, or cardiac cachexia between the two groups.

The blood samples were collected prospectively as part of the original study protocol. The lipid determinations were obtained at baseline, and at 6 months and 30 months post-infarction with consistent lipid lowering effects with Type IA agents at all three time periods. All specimens were analyzed in blinded fashion at a core lipid research laboratory that had no pre-existing knowledge of any clinical or laboratory information during the conduct of the trial that could have in any way biased the results of the current analysis.

In summary, this example shows that the long-term administration of Type IA antiarrhythmic medications to patients is associated with significant reductions in serum total cholesterol, triglyceride, Apo A-II, and Apo B levels. These reductions were independent of age, gender, body weight, diabetes, smoking status, concomitant medications, and a variety of measured covariates relating to the severity of the index infarct event. Therefore, Type IA antiarrhythmic agents are believed to represent a new class of hypolipidemic agent.

All patents and publications cited hereinabove are incorporated by reference herein. The invention has been described with reference to various specific and preferred embodiments and techniques. However, it should be understood that many variations and modifications may be made while remaining within the spirit and scope of the invention.

What is claimed is:

1. A therapeutic method of treatment for lowering the concentration of a serum lipid or lipid component comprising administering an amount of a Type IA antiarrhythmic agent to a mammal in need of such treatment, which amount is effective to lower the serum concentration of a lipid or a lipid component selected from the group consisting of cholesterol, total triglycerides, apoprotein $\beta$ and low-density lipoprotein-cholesterol in said mammal.

2. The method of claim 1 wherein the mammal is a human.

3. The method of claim 1 wherein the agent is administered orally.

4. The method of claim 1 wherein the Type IA antiarrhythmic agent is quinidine or a pharmaceutically acceptable salt thereof.

5. The method of claim 4 wherein the agent is quinidine gluconate, quinidine polygalacturonate or quinidine sulfate.

6. The method of claim 1 wherein the Type IA antiarrhythmic agent is procainamide or a pharmaceutically acceptable salt thereof.

7. The method of claim 6 wherein the agent is procainamide hydrochloride.

8. The method of claim 1 wherein the Type IA antiarrhythmic agent is disopyramide or a pharmaceutically acceptable salt thereof.

9. The method of claim 8 wherein the agent is disopyramide phosphate.

10. The method of claim 4 wherein quinidine or a pharmaceutically acceptable salt thereof is administered to a human at about 400 mg-2.0 g/day.

11. The method of claim 8 wherein disopyramide or a pharmaceutically acceptable salt thereof is administered to a human at about 150-600 mg./day.

12. The method of claim 6 wherein procainamide or a pharmaceutically acceptable salt thereof is administered to a human at about 1.0-4.5 g/day.

13. The method of claim 2 wherein the serum cholesterol is lowered about 5-15%.

14. The method of claim 2 wherein the total serum triglycerides are lowered about 12-35%.

15. The method of claim 2 wherein the serum apoprotein B is lowered about 7.5-20%.

16. The method of claim 1 wherein the agent is administered parenterally.

17. The method of claim 15 wherein the agent is administered intravenously.

* * * * *